United States Patent

Irie

(10) Patent No.: US 9,995,672 B2
(45) Date of Patent: Jun. 12, 2018

(54) FLUID-BORNE MICROORGANISM PARTICLE DETECTING DEVICE AND FLUID-BORNE MICROORGANISM PARTICLE DETECTING METHOD

(71) Applicant: Azbil Corporation, Tokyo (JP)

(72) Inventor: Kanami Irie, Tokyo (JP)

(73) Assignee: Azbil Corporation, Tokyo (JP)

( * ) Notice: Subject to any disclaimer, the term of this patent is extended or adjusted under 35 U.S.C. 154(b) by 30 days.

(21) Appl. No.: 15/258,313

(22) Filed: Sep. 7, 2016

(65) Prior Publication Data

US 2017/0074795 A1    Mar. 16, 2017

(30) Foreign Application Priority Data

Sep. 10, 2015 (JP) ................. 2015-178890

(51) Int. Cl.
| | |
|---|---|
| C12M 1/34 | (2006.01) |
| G01N 21/03 | (2006.01) |
| G01N 21/64 | (2006.01) |
| G01N 15/14 | (2006.01) |
| G01N 15/00 | (2006.01) |
| G01N 1/44 | (2006.01) |
| G01N 21/05 | (2006.01) |

(52) U.S. Cl.
CPC ..... *G01N 21/0332* (2013.01); *G01N 15/1404* (2013.01); *G01N 15/1459* (2013.01); *G01N 21/6486* (2013.01); *G01N 1/44* (2013.01); *G01N 21/05* (2013.01); *G01N 2015/0065* (2013.01)

(58) Field of Classification Search
CPC .................................................. C12M 1/3476
See application file for complete search history.

(56) References Cited

U.S. PATENT DOCUMENTS

2011/0216953 A1*  9/2011  Callahan .................. G06K 9/00
                                                                    382/128

FOREIGN PATENT DOCUMENTS

| JP | H08-29331 A | 2/1996 |
|---|---|---|
| JP | 2011-83214 | 4/2011 |
| JP | 5215522 B2 | 8/2013 |
| JP | 2014-153199 A | 8/2014 |

OTHER PUBLICATIONS

English (Google Patent) translation of Rion Co. Ltd., JP 2014-153199 A.*
Hasegawa, Norio, et al., "Instantaneous Bioaerosol Detection Technology and Its Application", Yamatake Corporation, Azbil Technical Review, Dec. 2009, pp. 2-7, 2009.

* cited by examiner

*Primary Examiner* — Rosanne Kosson
(74) *Attorney, Agent, or Firm* — Oblon, McClelland, Maier & Neustadt, L.L.P.

(57) ABSTRACT

A fluid-borne microorganism particle detecting device having a heating flow path wherein flows a liquid that includes a microorganism particle; a microwave emitting device for irradiating, with microwave radiation, the liquid that includes the microorganism particles within the heating flow path; an inspection flow path that is connected to the heating flow path; an excitation beam light source for emitting an excitation beam toward the inspection flow path; and a fluorescence detector for detecting fluorescent light emitted by microorganism particles in the inspection flow path that has been illuminated by the excitation beam.

10 Claims, 16 Drawing Sheets

FLUID-BORNE MICROORGANISM PARTICLE DETECTING DEVICE AND FLUID-BORNE MICROORGANISM PARTICLE DETECTING METHOD

CROSS-REFERENCE TO RELATED APPLICATION

This application claims priority to Japanese Application No. 2015-178890 filed Sep. 10, 2015. This application is incorporated herein in its entirety.

TECHNICAL FIELD

The present disclosure relates to an environmental technology, and, in particular, to a fluid-borne microorganism particle detecting device and a fluid-borne microorganism particle detecting method.

BACKGROUND

In clean rooms, such as bio clean rooms, airborne microorganism particles and non-microorganism particles are detected and recorded using particle detecting devices (referencing, for example, Japanese Unexamined Patent Application Publication No. 2011-83214; Japanese Patent No. 5275522, and N. Hasegawa, et al., "Instantaneous Bioaerosol Detection Technology and Its Application," Yamatake Corporation, Azbil Technical Review, December 2009, Pages 2-7, 2009). The state of wear of the air-conditioning equipment of the clean room can be ascertained from the result of the particle detection. Moreover, a record of particle detection within the clean room may be added as reference documentation to the products manufactured within the clean room. Optical particle detecting devices draw in air from a clean room, for example, and illuminate the drawn-in air with light. If a microorganism particle or non-microorganism particle is included in the air, then the particle that is illuminated by the light will produce florescent light or scattered light will be produced by the particle. Because of this, it is possible to detect the numbers and sizes of microorganism particles and non-microorganism particles that are included in a gas, through detecting the fluorescent and scattered light. Moreover, a technology able to detect accurately particles in not just clean rooms, but in fluids as well, is desired (referencing, for example, Japanese Unexamined Patent Application Publication No. H8-29331; Japanese Unexamined Patent Application Publication No. 2014-153199).

SUMMARY

There is a problem in that the fluorescent light emitted by fluid-borne microorganism particles is weak. Given this, one object of the present disclosure is to provide a fluid-borne microorganism particle detecting device and a fluid-borne microorganism particle detecting method able to detect fluid-borne microorganism particles accurately.

One aspect of the present disclosure provides a fluid-borne microorganism particle detecting device having (a) a heating flow path wherein flows a liquid that includes a microorganism particle; (b) a microwave emitting device for irradiating, with microwave radiation, the liquid that includes the microorganism particles within the heating flow path; (c) an inspection flow path that is connected to the heating flow path; (d) an excitation beam light source for emitting an excitation beam toward the inspection flow path; and (e) a fluorescence detector for detecting fluorescent light emitted by microorganism particles in the inspection flow path that has been illuminated by the excitation beam.

The fluid-borne microorganism particle detecting device may further include a recirculating flow path for returning, to the heating flow path, the liquid that includes microorganism particles, after flowing through the inspection flow path. Moreover, prior to recirculation by the recirculating flow path, the microwave emitting device may refrain from irradiating, with microwave radiation, the liquid that includes the microorganism particles. Moreover, after recirculation by the recirculating flow path, the microwave emitting device may irradiate, with microwave radiation, the liquid that includes the microorganism particles.

The fluid-borne microorganism particle detecting device may further have a before/after comparing portion for comparing intensities of fluorescent light emitted by particles prior to recirculation by the recirculating flow path and intensities of fluorescent light emitted by the particles after recirculation by the recirculating flow path.

In the fluid-borne microorganism particle detecting device, the heating flow path may be a peak with respect to light.

Moreover, one aspect of the present disclosure provides a fluid-borne microorganism particle detecting method including: (a) irradiation, with microwave radiation, of a liquid that includes microorganism particles; and (b) illumination, by an excitation beam, of the microorganism particles that have been irradiated with the microwave radiation, and detection of fluorescent light emitted by the microorganism particles.

The fluid-borne microorganism particle detecting method may further include, prior to irradiation, with microwave radiation, of a liquid that includes microorganism particles, illumination, with an excitation beam, of microorganism particles that have not been irradiated with the microwave radiation, and detection of fluorescent light emitted by the microorganism particles.

The fluid-borne microorganism particle detecting method may further include comparison of intensities of fluorescent light emitted by particles that have not been irradiated with the microwave radiation and intensities of fluorescent light emitted by particles that have been irradiated with the microwave radiation. Moreover, in the fluid-borne microorganism particle detecting method, the particles may be evaluated as microorganism particles if the intensities of the fluorescent light emitted by the particles after irradiation with the microwave radiation are greater than the intensities of the fluorescent light emitted by the particles that have been irradiated with the microwave radiation.

The present disclosure enables the provision of a fluid-borne microorganism particle detecting device and fluid-borne microorganism particle detecting method able to detect fluid-borne microorganism particles accurately.

DETAILED DESCRIPTION

Examples of the present disclosure will be described below. Note that the descriptions and drawings that form a portion of the present disclosure should not be understood to be limiting the present disclosure. A variety of alternate technologies and application technologies should be clear, from the present disclosure, to a person skilled in the art, and it should be understood that the present disclosure includes a variety of embodiments, and the like, that are not described herein.

The fluid-borne microorganism particle detecting device according to the present examples includes a heating flow path 201 wherein flows a liquid that includes a microorganism particle; a microwave emitting device 202 for irradiating, with microwave radiation, the liquid that includes the microorganism particles within the heating flow path 201; an inspection flow path 40 that is connected to the heating flow path 201; an excitation beam light source 10 for emitting an excitation beam toward the inspection flow path 40; and a fluorescence detector 102 for detecting fluorescent light emitted by microorganism particles in the inspection flow path 40 that has been illuminated by the excitation beam. Here the microwave refers to electromagnetic radiation of a frequency between 300 MHz and 300 GHz.

The heating flow path 201 may be opaque to light, as long as it is transparent to microwave radiation. Given this, an opaque tough material may be used as the material for the heating flow path 201. When the liquid within the heating flow path 201 is irradiated, heat is produced through a dielectric loss. Moreover, when microorganism particles that exist within the fluid are irradiated microwave radiation with the microwave radiation, they are heated through dielectric loss. Note that in the liquid within the heating flow path 201 can be heated by microwave radiation even if it is turbid or opaque.

A Maillard reaction occurs in microorganism particles that are heated, through the solvent and internal fluid irradiated with the microwave radiation. A Maillard reaction is a reaction that produces an advanced glycation end product of (AGE) through heating of an amino compound, such as an amino acid, a peptide, a protein, or the like, in the presence of a saccharide, such as glycos, or the like. Advanced glycation end products produce fluorescent light. Note that even if no Maillard reaction occurs within the microorganism particle, the nicotinamide adenine dinucleotides, riboflavin, and the like within the microorganism particle will produce fluorescent light. However, in a microorganism particle wherein a Maillard reaction has occurred the advanced glycation end product also produces fluorescent light, and thus, when compared to a microorganism particle wherein no Maillard reaction has occurred, a microorganism particle wherein the Maillard reaction has occurred will produce fluorescent light with greater intensity.

Maillard reactions to not occur in non-microorganism particles since they do not include proteins or saccharides. Consequently, when the heating flow path 201 is irradiated with microwave radiation, there will be an increase in fluorescent substances in microorganism particles, but no increase in fluorescent substances in non-microorganism particles.

The heating flow path 201 has a length such that the liquid that includes the microorganism particles can pass through the microwave-illuminated region over the time required for the microwave irradiation to complete the Maillard reaction in a microorganism particle, for example. If the time required for the microwave irradiation to complete the Maillard reaction in a microorganism particle is 10 minutes, the heating flow path 201 will have a length such that the liquid that includes the microorganism particles will take 10 minutes to pass through the heating flow path 201. The length of the heating flow path is designed as appropriate depending on the inner diameter of the heating flow path 201, the flow speed of the liquid that includes the microorganism particles, and the intensity of the microwave radiation.

The heating flow path 201, in order to secure the required length, may be of, for example, a spiral shape, or may have a structure that is bent three-dimensionally. For the outer shape of the bent-back structure may form, for example, a rectangular solid shape, or may form a spherical shape. If the heating flow path 201 is made from a material that is transparent to microwave radiation, the interior of the structure that is bent-back three-dimensionally need not be visible from the outside.

The microwave emitting device 202 may be provided with a single-mode resonance resonator, or may be provided with a multi-mode resonance resonator. Moreover, the microwave radiation that is emitted by the microwave emitting device 202 may be reflected by a reflecting member, to adjust the region illuminated by the microwave radiation.

Figure 1:
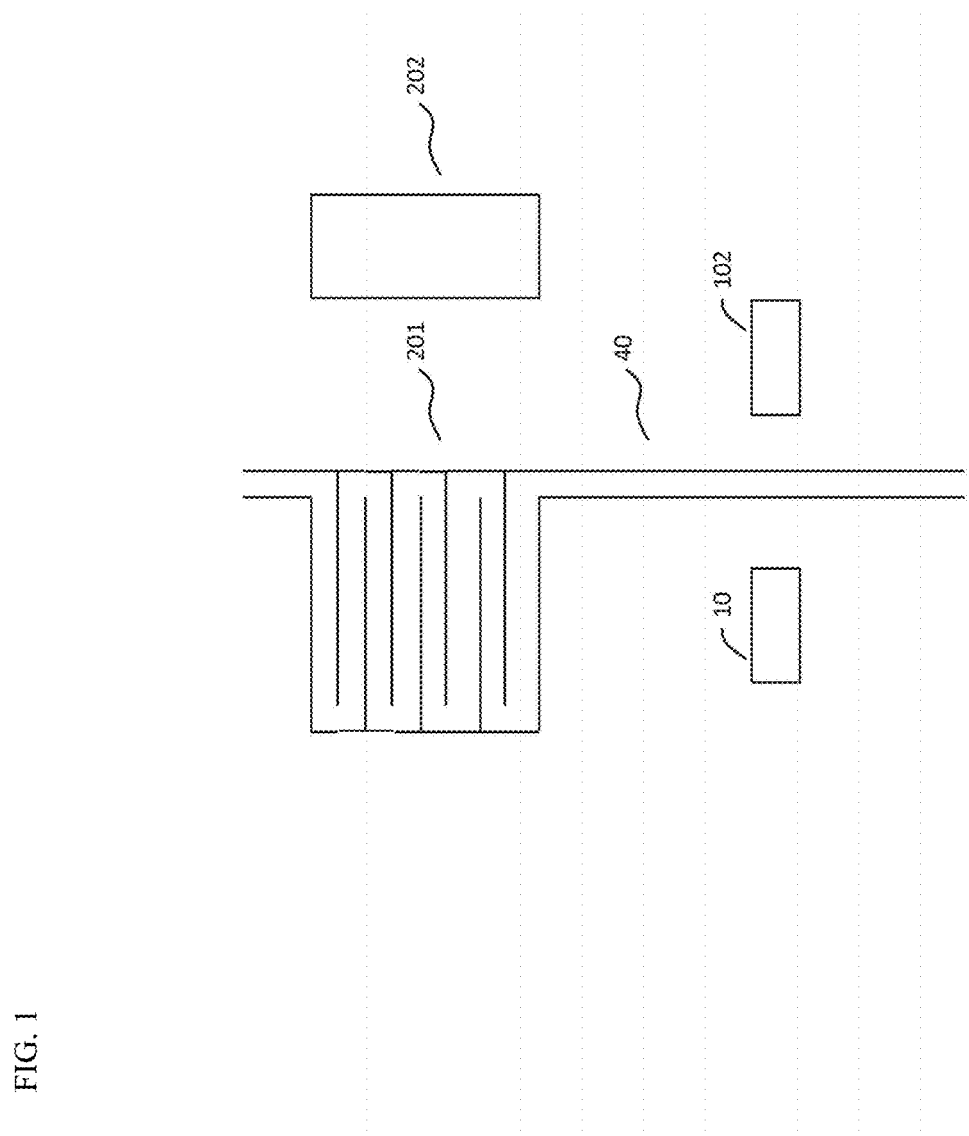
FIG. 1 is a schematic diagram of a fluid-born microorganism particle detecting device according to an example according to the present disclosure.
Figure 2:
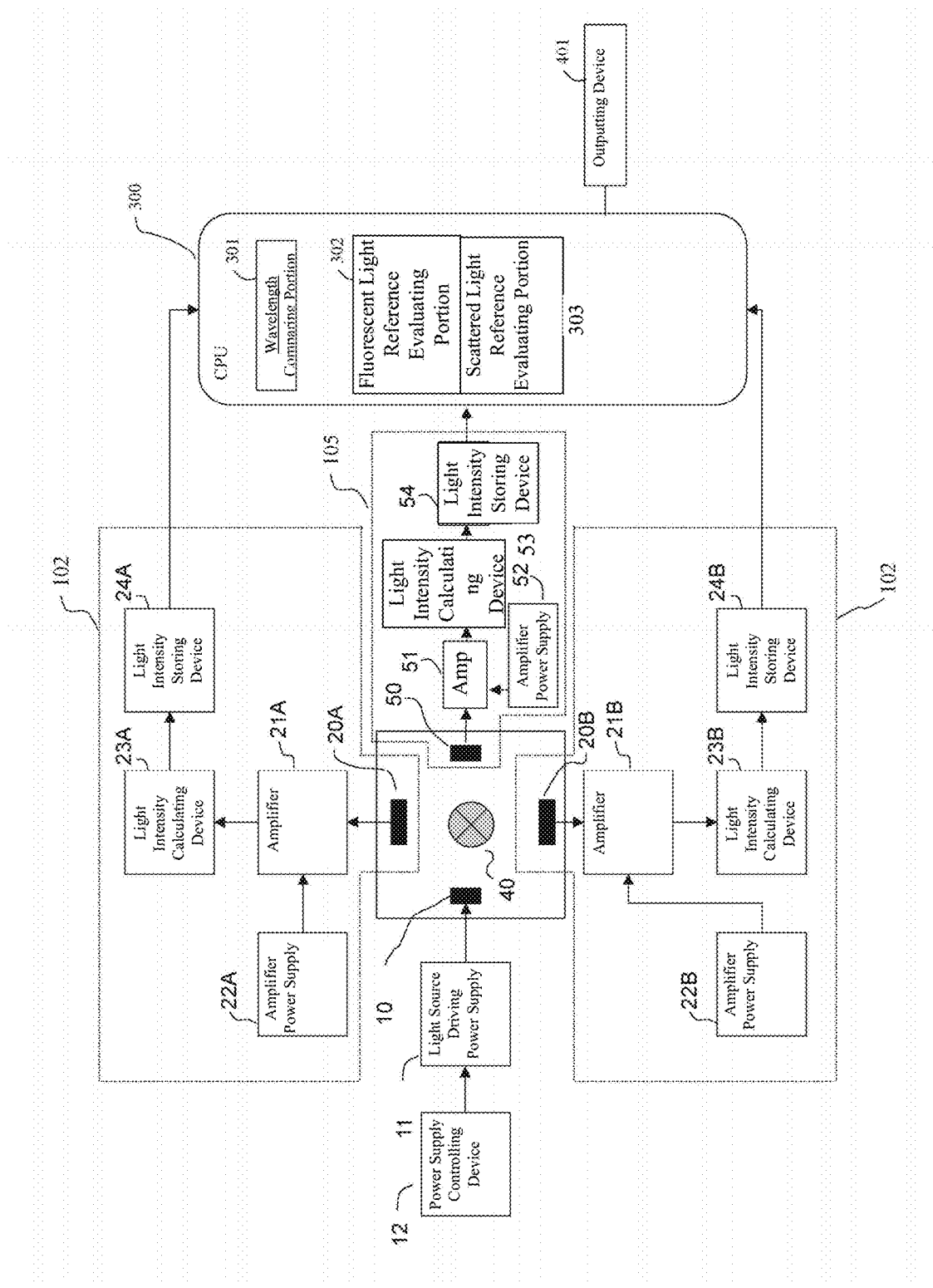
FIG. 2 is a schematic diagram of an optical system for a fluid-born microorganism particle detecting device according to an example according to the present disclosure.

As illustrated in FIG. 2, the fluid-borne microorganism detecting device may further be provided with a scattered light detector 105 for detecting scattered light of the same wavelength as the excitation beam, produced within the liquid illuminated by the excitation beam. A light source driving power supply 11 for supplying electric power to the excitation beam light source 10 is connected to the excitation beam light source 10. A power supply controlling device 12 for controlling the electric power that is supplied to the excitation beam light source 10 is connected to the light source driving power supply 11.

The excitation beam light source 10 emits an excitation beam of a broad wavelength band toward the liquid that flows within the inspection flow path 40. A light-emitting diode (LED) or a laser, for example, may be used for the excitation beam light source 10. The wavelength of the excitation beam may be, for example, between 250 and 550 nm. The excitation beam may be a visible light, or may be ultraviolet radiation. In the case of the excitation beam being visible light, the wavelength of the excitation beam is in the range of for example, between 400 and 550 nm, for example, 405 nm. In the case of the excitation beam being ultraviolet light, the wavelength of the excitation beam is in the range of for example, between 300 and 380 nm, for example, 340 nm. However, the wavelengths of the excitation beam are not limited thereto.

The inspection flow path 40 is made from, for example, quartz, which is transparent in respect to the excitation beam.

If here microorganisms, or the like, are included in the solution in the detection flow path 40, then the nicotinamide adenine dinucleotides, riboflavin, advanced glycation end products, and the like, that are included in the microorganisms that are illuminated by the excitation beam will emit florescent light. Moreover, even when non-microorganism particles made from, for example, metal or resin are included in the liquid within the inspection flow path 40, the non-microorganism particles that are illuminated by the excitation beam may emit fluorescent light or light having a wavelength band that overlaps that of the fluorescent light. Note that "fluorescence" includes auto-fluorescence. However, as described above, the Maillard reaction occurs in microorganism particles and does not occur in non-microorganism particles, and thus the increased intensity of the fluorescent light due to the Maillard reaction will not occur in non-microorganism particles.

For example, when the liquid is water that is manufactured by a purified water manufacturing device, non-microorganism particles that are made from the materials of the purified water manufacturing device may be present within the water. For example, particles made from materials that are one or more selections from polypropylene, polyethylene, polytetrafluoroethylene (PTFE), olefin, polycarbonate, polyurethane, and the like, may be produced from the filter or housing of the purified water manufacturing device. Moreover, particles made from materials that are one or more selections from, for example, silicon rubber, nitrile rubber (NBR), ethylenepropylene rubber (EPDM), fluorine rubber, kalrez, PTFE, and the like, may be produced by the packing that is provided in the purified water manufacturing device. Additionally, particles made from one or more selections from Viton, fluorine resins, silicon resins, polyamide, polyphenylene sulfide (PPS), perfluoro, and the like, may be produced from the pump that is provided in the purified water manufacturing device. Furthermore, particles of PTFE, or the like, may be produced from the seals that are installed in the purified water manufacturing device. In addition, particles made from metal materials, such as oxidized stainless steel, or the like, may be produced from the pipes in the purified water manufacturing device. When the materials of the particles that may be produced from the purified water manufacturing device, as described above, are illuminated by an excitation beam, in some cases they will produce florescent light or light having a wavelength band that overlaps that of fluorescent light.

The spectra of the light in the fluorescent bands emitted by the microorganisms and non-microorganism particles will vary depending on the type of microorganism or non-microorganism particle. Moreover, typically the intensity of light in the fluorescent wavelength band that is emitted by a microorganism tends to be more intense on the side of longer wavelengths than the intensity of light in the fluorescent wavelength band emitted by non-microorganism particles. Because of this, it is possible to evaluate whether a substance, such as a particle, that is included within a liquid is a microorganism or a non-microorganism particle based on intensities of light in the fluorescent band detected at a plurality of wavelengths.

The fluorescence detector 102 detects light in the fluorescent band produced by the microorganism particles or non-microorganism particles. The fluorescence detector 102 comprises: a first photodetecting element 20A for detecting light of a first fluorescent wavelength band; and a second photodetecting element 20B for detecting light of a second fluorescent wavelength band, different from that of the first fluorescent wavelength band, on the shorter wavelength side than that of the first fluorescent wavelength band. Photodiodes, photoelectron multiplier tubes, and the like, may be used for the first photodetecting element 20A and the second photodetecting element 20B, and, when light is detected, the optical energy is converted into electrical energy.

An amplifier 21A, for amplifying the current that is produced by the first photodetecting element 20A, is connected to the first photodetecting element 20A. An amplifier power supply 22A, for supplying electric power to the amplifier 21A, is connected to the amplifier 21A. Moreover, a light intensity calculating device 23A, for calculating the intensity of light detected by the first photodetecting element 20A, by detecting the current that has been amplified by the amplifier 21A, is connected to the amplifier 21A. A light intensity calculating device 23A calculates light intensity based on, for example, the area of the spectrum of the light that is detected. A light intensity storing device 24A, for storing the intensity of light calculated by the light intensity calculating device 23A, is connected to the light intensity calculating device 23A.

An amplifier 21B, for amplifying the current that is produced by the second photodetecting element 20B, is connected to the second photodetecting element 20B. An amplifier power supply 22B, for supplying electric power to the amplifier 21B, is connected to the amplifier 21B. Moreover, a light intensity calculating device 23B, for calculating the intensity of light detected by the second photodetecting element 20B, by detecting the current that has been amplified by the amplifier 21B, is connected to the amplifier 21B. A light intensity calculating device 23B calculates light intensity based on, for example, the area of the spectrum of the light that is detected. A light intensity storing device 24B, for storing the intensity of light calculated by the light intensity calculating device 23B, is connected to the light intensity calculating device 23B.

The scattered light detector 105 detects scattered light produced by a microorganism particle or non-microorganism particle illuminated by the inspecting light. The scattered light detector 105 comprises a scattered light photodetecting element 50 for detecting scattered light. A photodiode, or the like, may be used for the scattered light photodetecting element 50, to convert light energy into electrical energy when light is detected.

An amplifier 51 for amplifying the current produced by the scattered light photodetecting element 50 is connected to the scattered light photodetecting element 50. An amplifier power supply 52 for supplying electric power to the amplifier is connected to the amplifier 51. Moreover, a light intensity calculating device 53 for calculating the intensity of the scattered light detected by the scattered light photodetecting element 50 by detecting the current that is amplified by the amplifier 51 is connected to the amplifier 51. A light intensity storing device 54 for storing the intensity of the scattered light that is calculated by the light intensity calculating device 53 is connected to the light intensity calculating device 53.

When there is a liquid flowing within the inspection flow path 40, the excitation beam light source 10 emits an excitation beam, the fluorescence detector 102 measures a light intensity in a first fluorescent wavelength band and a light intensity in a second fluorescent wavelength band, and stores them, in a time series, in light intensity storing devices 24A and 24B. Moreover, the scattered light detector 105 measures the scattered light and stores the light intensities of the scattered light in a time series in a light intensity storing device 54.

The fluid-borne microorganism particle detecting device according to the first embodiment further includes a central calculation processing device (CPU) 300. The CPU 300 includes a scattered light reference evaluating portion 303. The scattered light reference evaluating portion 303 reads out, from the light intensity storing devices 24A and 24B, a value for the light intensity in the first fluorescent wavelength band and a value for the light intensity in the second fluorescent wavelength band. Moreover, the scattered light reference evaluating portion 303 reads out a scattered light intensity from the light intensity storing device 54.

The scattered light reference evaluating portion 303 evaluates that there is a bubble in the water that is subject to inspection if the scattered light detector 105 has measured scattered light without the fluorescence detector 102 measuring light in the fluorescent band. Moreover, the scattered light reference evaluating portion 303 may evaluate that the water that is subject to inspection includes neither microorganisms nor non-microorganism particles if the scattered light detector 105 has measured scattered light without the fluorescence detector 102 measuring light in the fluorescent band. Moreover, the scattered light reference evaluating portion 303 may evaluate that the water that is subject to inspection includes microorganisms or non-microorganism particles if the fluorescence detector 102 has measured light in the fluorescent band and the scattered light detector 105 has measured scattered light.

The CPU 300 may further include a wavelength comparing portion 301 and a fluorescent light reference evaluating portion 302. The wavelength comparing portion 301 reads out, from the light intensity storing devices 24A and 24B, values for the light intensity in the first fluorescent wavelength band and values for the light intensity in the second fluorescent wavelength band that have been detected. Moreover, the wavelength comparing portion 301 compares the light intensity in the first fluorescent wavelength band and the light intensity in the second fluorescent wavelength band. If the light intensity in the first fluorescent wavelength band, which is on the long wavelength side, are greater than the light intensity in the second fluorescent wavelength band, which is on the short wavelength side, the fluorescent light reference evaluating portion 302 evaluates that microorganisms are included in the liquid. Moreover, if the light intensity in the second fluorescent wavelength band, which is on the short wavelength side, are greater than the light intensity in the first fluorescent wavelength band, which is on the long wavelength side, then the fluorescent light reference evaluating portion 302 evaluates that the liquid includes non-microorganism particles.

The fluorescent light reference evaluating portion 302 outputs the evaluation result from, for example, an outputting device 401. A display, a speaker, a printer, or the like, may be used for the outputting device 401.

The fluid-borne microorganism particle detecting device according to the first embodiment, described above, enables an increase in the intensity of the fluorescent light that is emitted by microorganism particles through microwave irradiation. Typically the fluorescent light that is emitted by microorganism particles prior to the occurrence of a Maillard reaction is weak, and when the intensities of the fluorescent light that are emitted by the microorganism particles is increased through microwave irradiation, this can improve the accuracy with which the microorganism particles are detected. Moreover, because the Maillard reaction does not occur in non-microorganism particles, this enables the intensity of the fluorescent light of the microorganism particles to be increased selectively through microwave irradiation.

Figure 3:
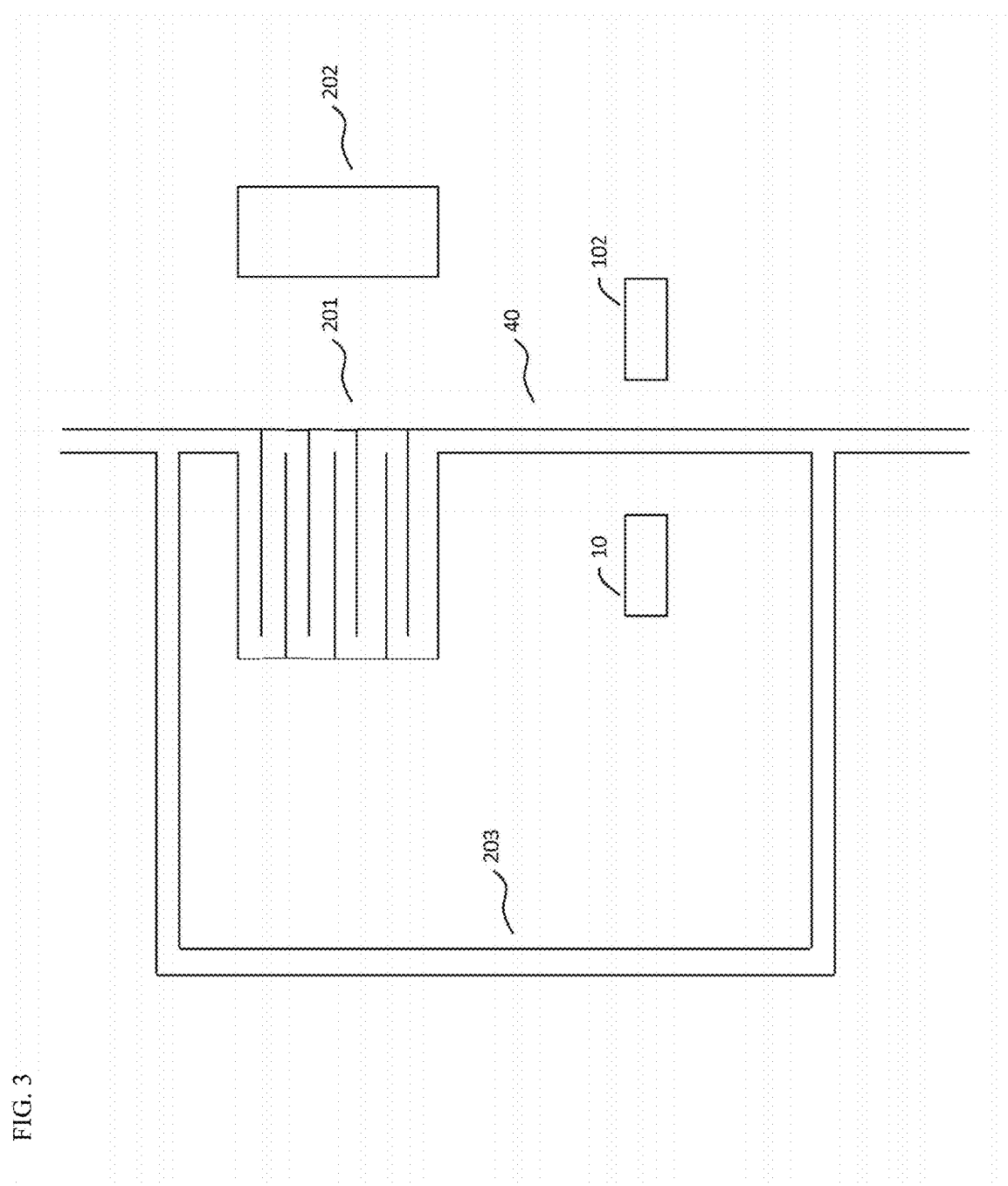
FIG. 3 is a schematic diagram of a fluid-born microorganism particle detecting device according to another example according to the present disclosure.

A fluid-borne microorganism particle detecting device according to a second embodiment further comprises a recirculating flow path 203 that returns, to the heating flow path 201, the liquid that includes the microorganism particles that are flowing within the inspection flow path 40, as illustrated in FIG. 3. In another example, the microwave emitting device 202 will not irradiate, with microwave radiation, the liquid within the heating flow path 201 even though the liquid that includes microorganism particles, prior to recirculation in the recirculating flow path 203, is flowing through the heating flow path 201. However, the microwave emitting device 202 irradiates, with microwave radiation, the liquid within the heating flow path 201 when the liquid that includes the microorganism particles is flowing in the heating flow path 201 after having been recirculated by the recirculating flow path 203.

Figure 4:
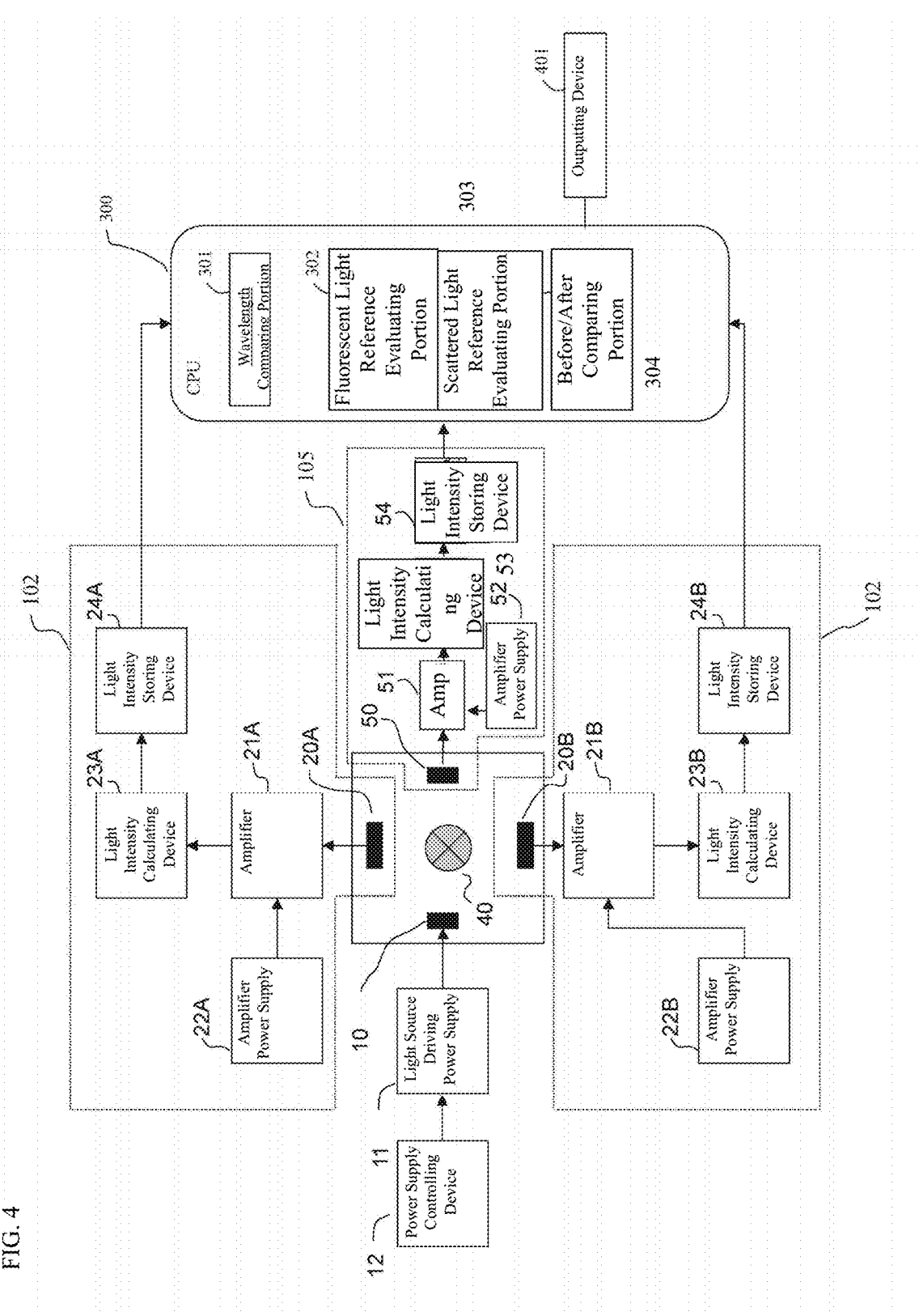
FIG. 4 is a schematic diagram of an optical system for a fluid-born microorganism particle detecting device according to another example according to the present disclosure.

In this example, as illustrated in FIG. 4, the CPU 300 further includes a before/after comparing portion 304 for comparing the intensities of fluorescent light emitted by particles prior to recirculation by the recirculating flow path 203 and the intensities of fluorescent light emitted by particles after recirculation by the recirculating flow path 203.

The before/after comparing portion 304 determines that the particles are non-microorganism particles if the intensities of the fluorescent light emitted by the particles that have not been irradiated with microwave radiation, prior to recirculation by the recirculating flow path 203, are equal to the intensities of the fluorescent light emitted by particles that have been irradiated with microwave radiation, after recirculation by the recirculating flow path 203. Moreover, the before/after comparing portion 304 determines that the particles are microorganism particles if the intensities of the fluorescent light emitted by the particles that have been irradiated with microwave radiation, after recirculation by the recirculating flow path 203, are greater than the intensities of the fluorescent light emitted by particles that have not been irradiated with microwave radiation, prior to recirculation by the recirculating flow path 203.

The fluid-borne microorganism particle detecting device according to another example enables microorganism particles to be identified more accurately vis-à-vis a non-microorganism particles.

While there are descriptions of examples as set forth above, the descriptions and drawings that form a portion of the disclosure are not to be understood to limit the present disclosure. A variety of alternate examples of embodiment and operating technologies should be obvious to those skilled in the art. While, for example, in the embodiment an example was shown wherein the intensities of the fluorescent light of a plurality of wavelength bands were detected by a plurality of photodetecting elements, the intensity of the fluorescent light in a single wavelength band may be detected by a single photodetecting element instead. In this way, the present disclosure should be understood to include a variety of embodiments, and the like, not set forth herein.

EXAMPLES

Example 1

Figure 5:
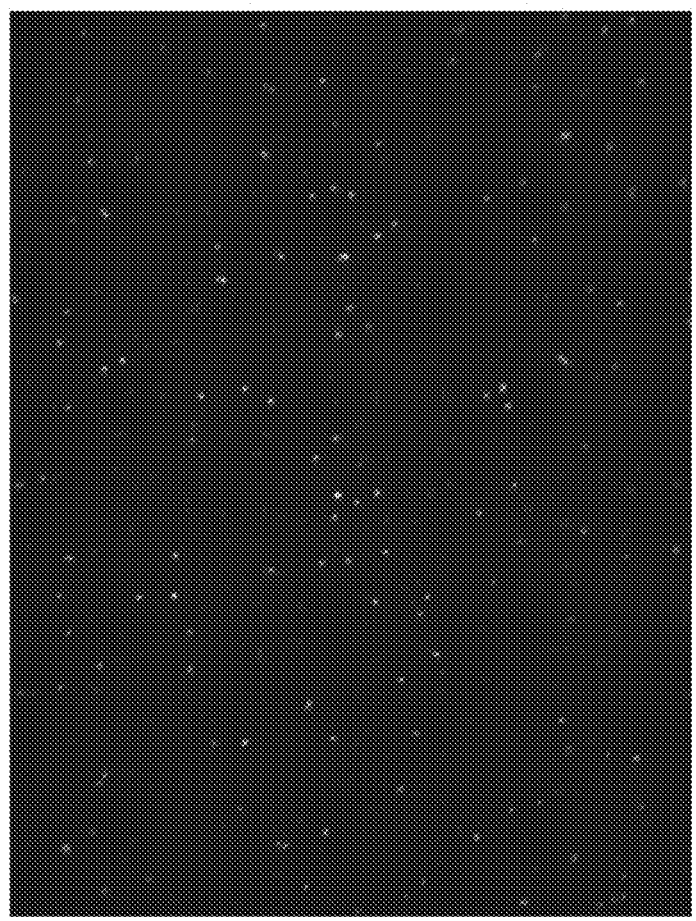
FIG. 5 is a fluorescent image of a *Staphylococcus epidermidis* suspension that has not been irradiated with microwave radiation, according to an example according to the present disclosure.
Figure 6:
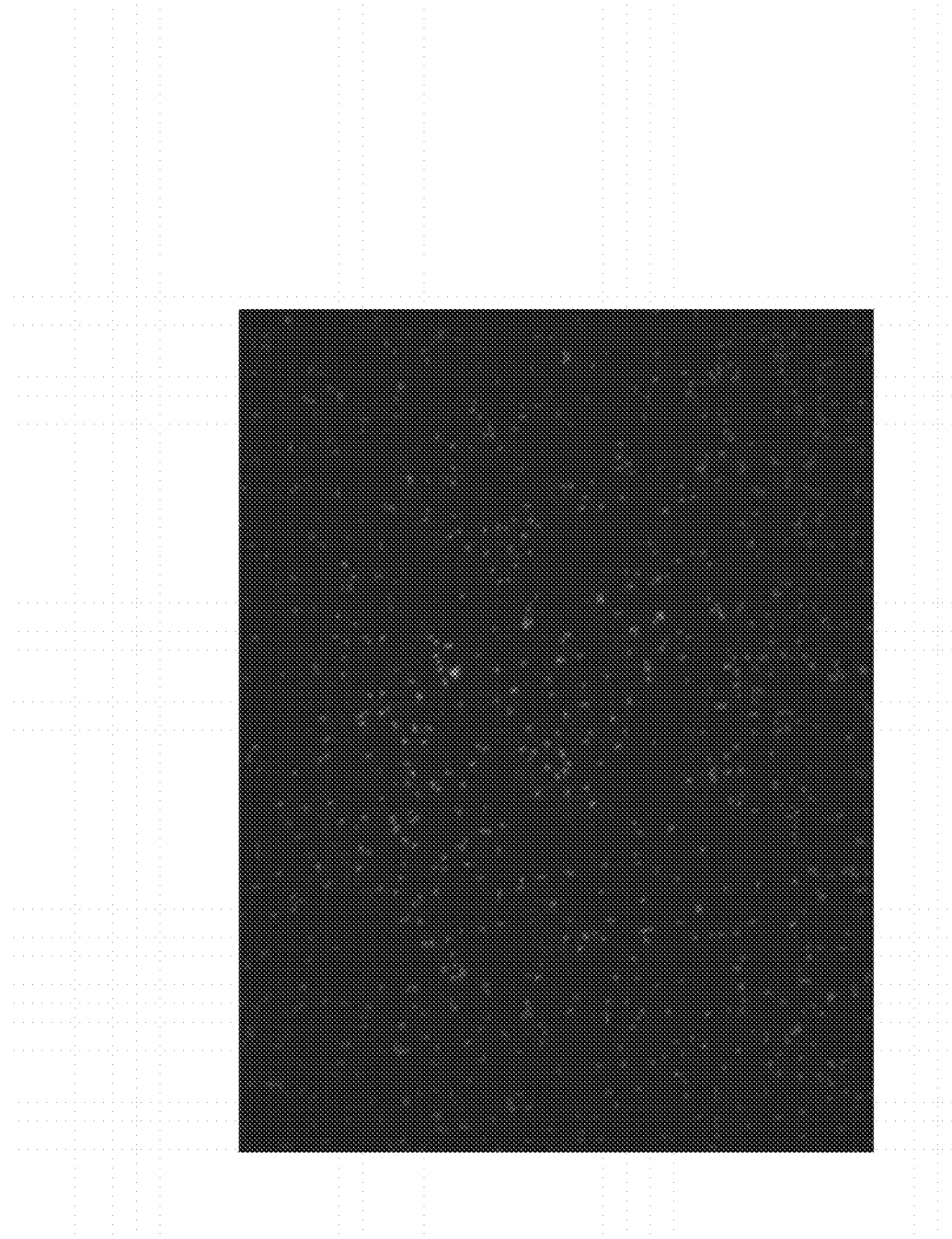
FIG. 6 is a fluorescent image of a *Staphylococcus epidermidis* suspension that has been irradiated with microwave radiation, according to the example according to the present disclosure.
Figure 7:
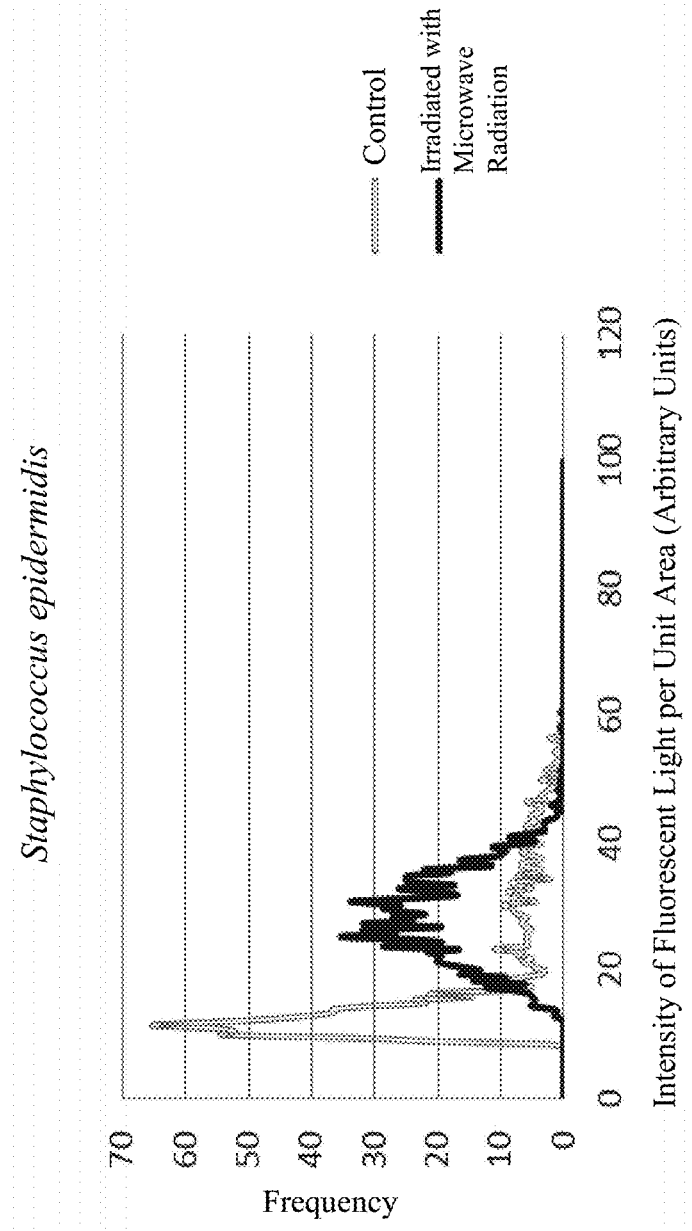
FIG. 7 is a histogram of the fluorescent light intensity distribution of a *Staphylococcus epidermidis* suspension that has not been irradiated with microwave radiation, and a histogram of the fluorescent light intensity distribution of a *Staphylococcus epidermidis* suspension that has been irradiated with microwave radiation, according to the example according to the present disclosure.

A single-mode resonance resonator was used to irradiate a 3 mL suspension of *Staphylococcus epidermidis* for 10 minutes with a 400 W microwave. At this time, the single-mode resonance resonator was controlled so that the temperature of the suspension would not exceed 200° C. Thereafter, a *Staphylococcus epidermidis* suspension that has not been irradiated with the microwave radiation (a control) and the *Staphylococcus epidermidis* suspension that has been irradiated with the microwave radiation were dripped onto respective slide glasses and observed under a fluorescent microscope. The result was the production of the control fluorescent image shown in FIG. 5 and the fluorescent image of the *Staphylococcus epidermidis* suspension that has been irradiated with microwave radiation, shown in FIG. 6. Moreover, when the fluorescent images were analyzed and histograms of the intensities of fluorescent light were produced, the fluorescent intensities of the *Staphylococcus epidermidis* suspension that was irradiated with microwave radiation showed greater intensities than the control, as illustrated in FIG. 7.

Example 2

Figure 8:
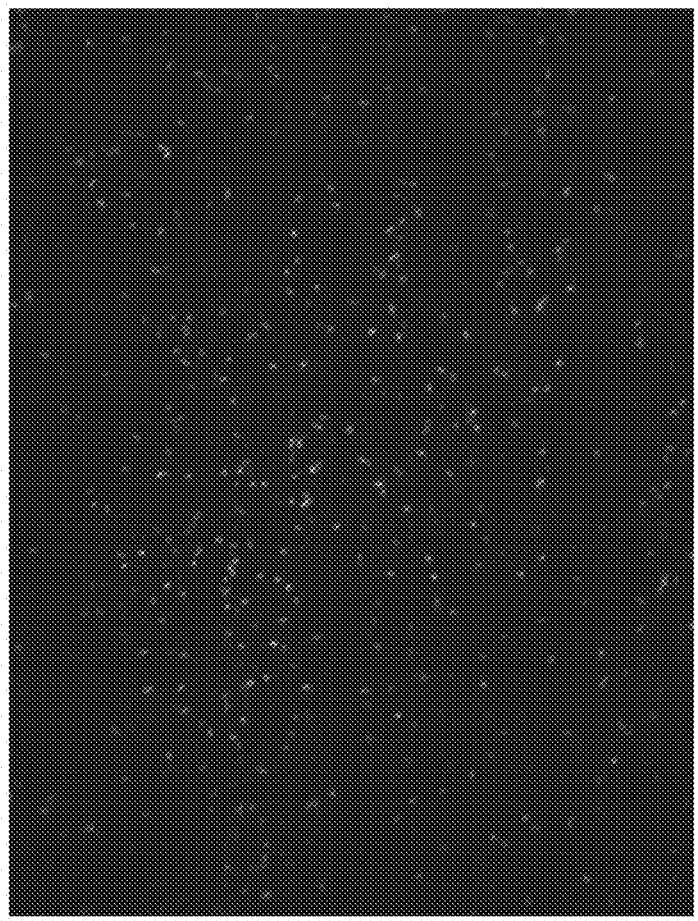
FIG. 8 is a fluorescent image of an *Escherichia coli* suspension that has not been irradiated with microwave radiation, according to another example according to the present disclosure.
Figure 9:
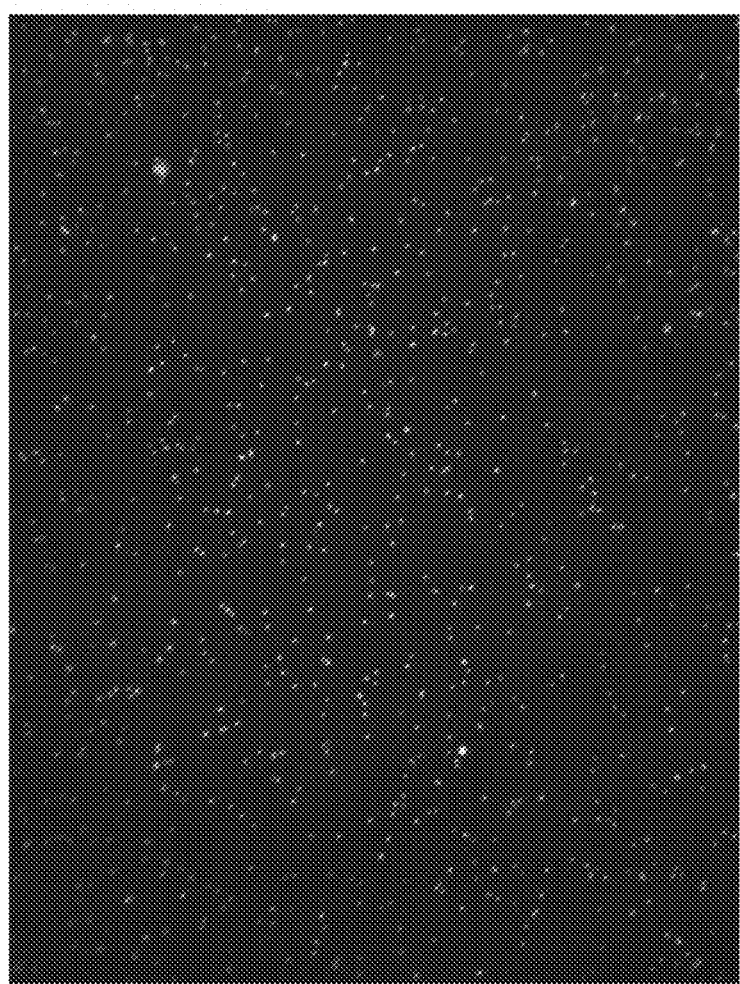
FIG. 9 is a fluorescent image of an *Escherichia coli* suspension that has been irradiated with microwave radiation, according to another example according to the present disclosure.
Figure 10:
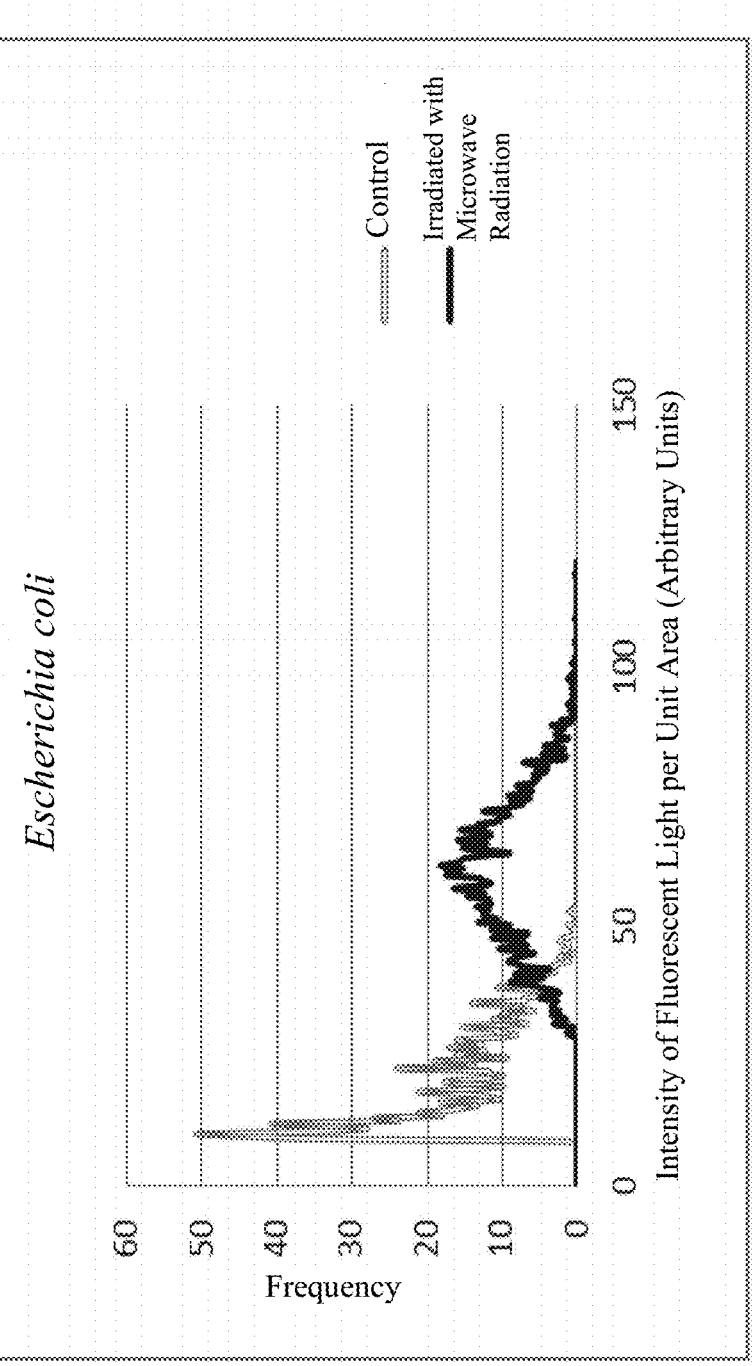
FIG. 10 is a histogram of the fluorescent light intensity distribution of a *Escherichia coli* suspension that has not been irradiated with microwave radiation, and a histogram of the fluorescent light intensity distribution of a *Escherichia coli* suspension that has been irradiated with microwave radiation, according to another example according to the present disclosure.

A single-mode resonance resonator was used to irradiate a 3 mL suspension of *Escherichia coli* for 10 minutes with a 400 W microwave. At this time, the single-mode resonance resonator was controlled so that the temperature of the suspension would not exceed 200° C. Thereafter, a *Escherichia coli* suspension that has not been irradiated with the microwave radiation (a control) and the *Escherichia coli* suspension that has been irradiated with the microwave radiation were dripped onto respective slide glasses and observed under a fluorescent microscope. The result was the production of the control fluorescent image shown in FIG. 8 and the fluorescent image of the *Escherichia coli* suspension that has been irradiated with microwave radiation, shown in FIG. 9. Moreover, when the fluorescent images were analyzed and histograms of the intensities of fluorescent light were produced, the fluorescent intensities of the *Escherichia coli* suspension that was irradiated with microwave radiation showed greater intensities than the control, as illustrated in FIG. 10.

Comparative Example 1

Figure 11:
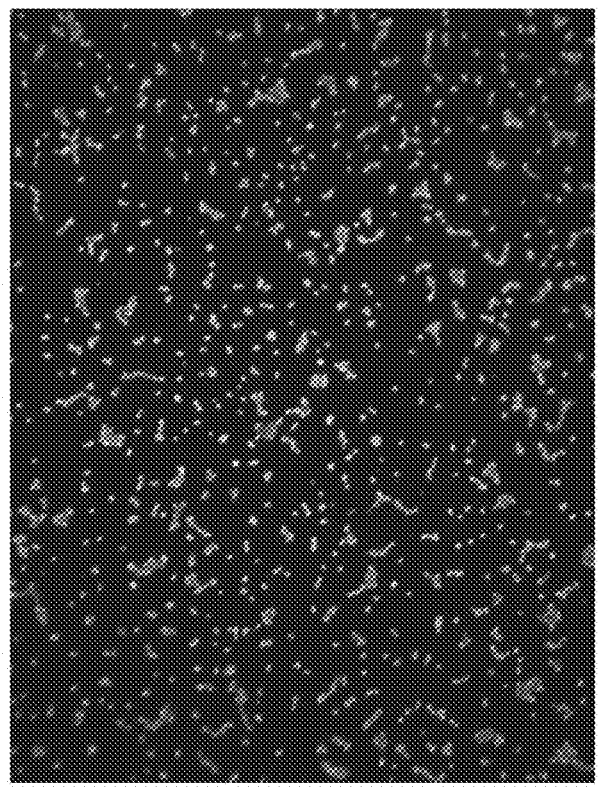
FIG. 11 is a fluorescent image of dried *Staphylococcus epidermidis* that has not been irradiated with microwave radiation, according to a first comparative example of the present disclosure.
Figure 12:
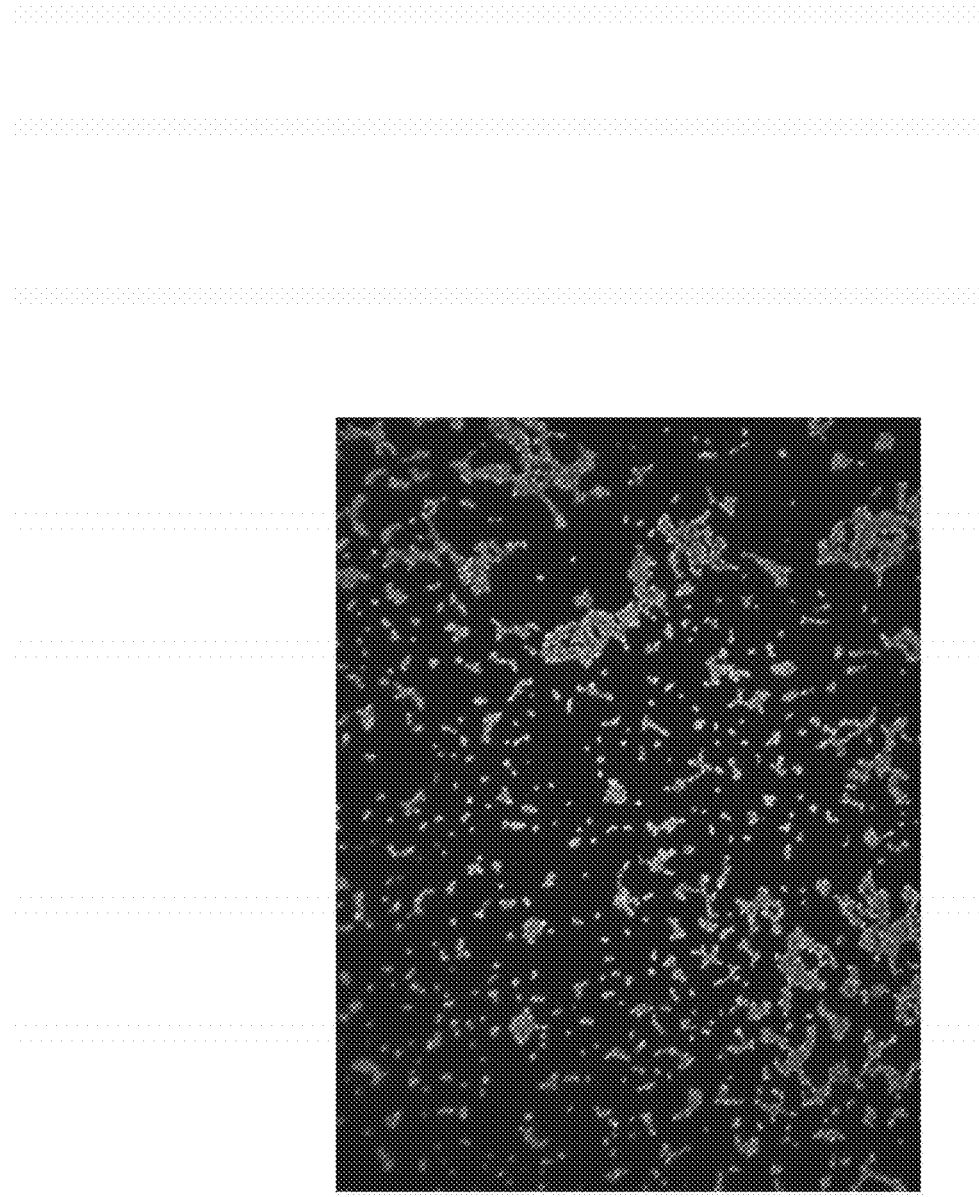
FIG. 12 is a fluorescent image of dried *Staphylococcus epidermidis* that has been irradiated with microwave radiation, according to a first comparative example of the present disclosure.
Figure 13:
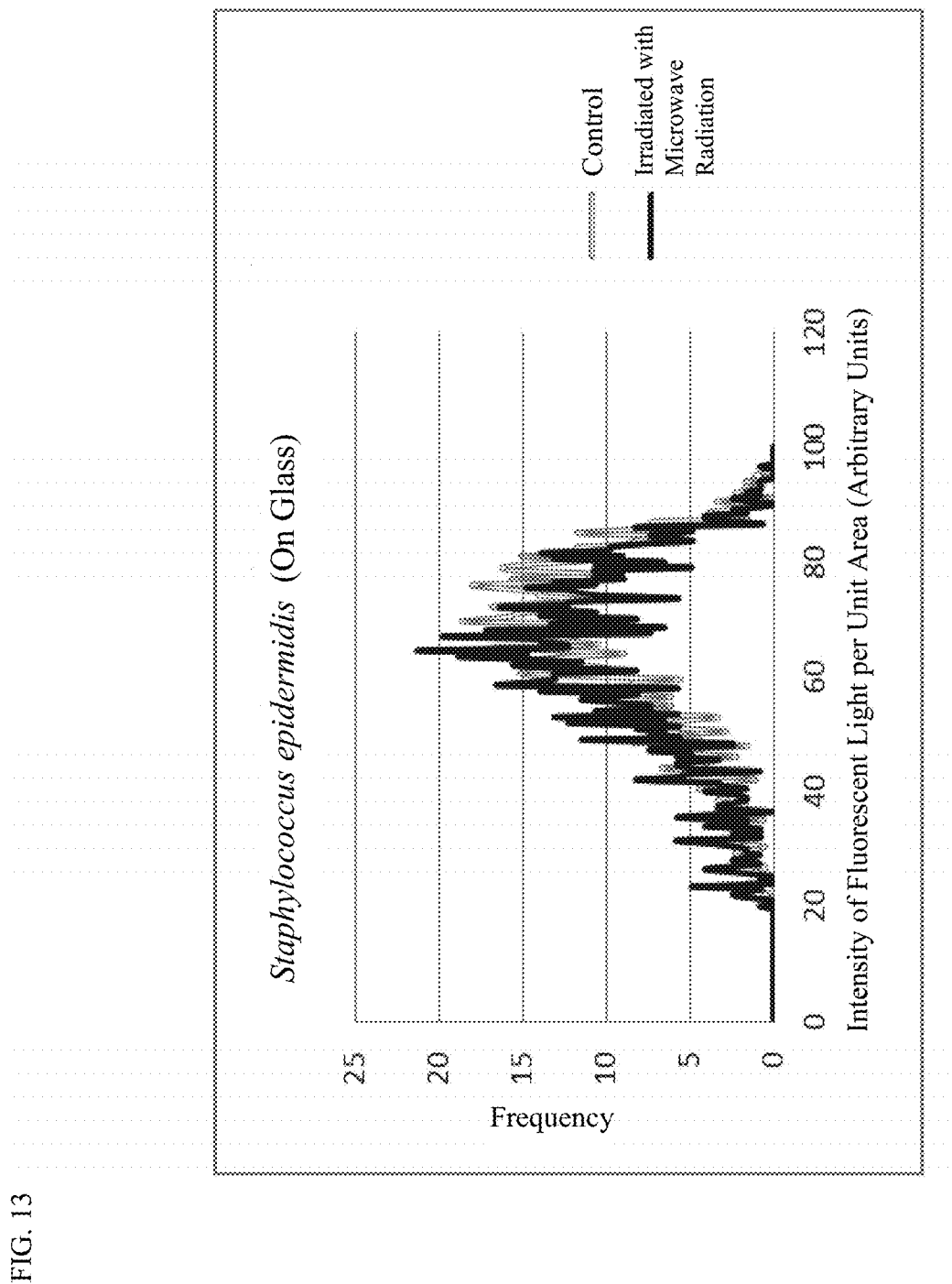
FIG. 13 is a histogram of the fluorescent light intensity distribution of dried *Staphylococcus epidermidis* that has not been irradiated with microwave radiation, and a histogram of the fluorescent light intensity distribution of dried *Staphylococcus epidermidis* that has been irradiated with microwave radiation, according to a first comparative example of the present disclosure.

A single-mode resonance resonator was used to irradiate naturally dried *Staphylococcus epidermidis* on a slide glass for 10 minutes with a 400 W microwave, but no increase in temperature was seen. Thereafter, naturally dried *Staphylococcus epidermidis* on a slide glass that has not been irradiated with the microwave radiation (a control) and the naturally dried *Staphylococcus epidermidis* on the slide glass that has been irradiated with the microwave radiation were observed under a fluorescent microscope. The result was the production of the control fluorescent image, shown in FIG. 11, and the fluorescent image of dried *Staphylococcus epidermidis* that has been irradiated with microwave radiation, shown in FIG. 12. Moreover, when the fluorescent images were analyzed and histograms of the intensities of fluorescent light were produced, no significant difference was seen between the fluorescent intensities of the dried *Staphylococcus epidermidis* that was irradiated with microwave radiation when compared to those in the control, as illustrated in FIG. 13.

Comparative Example 2

Figure 14:
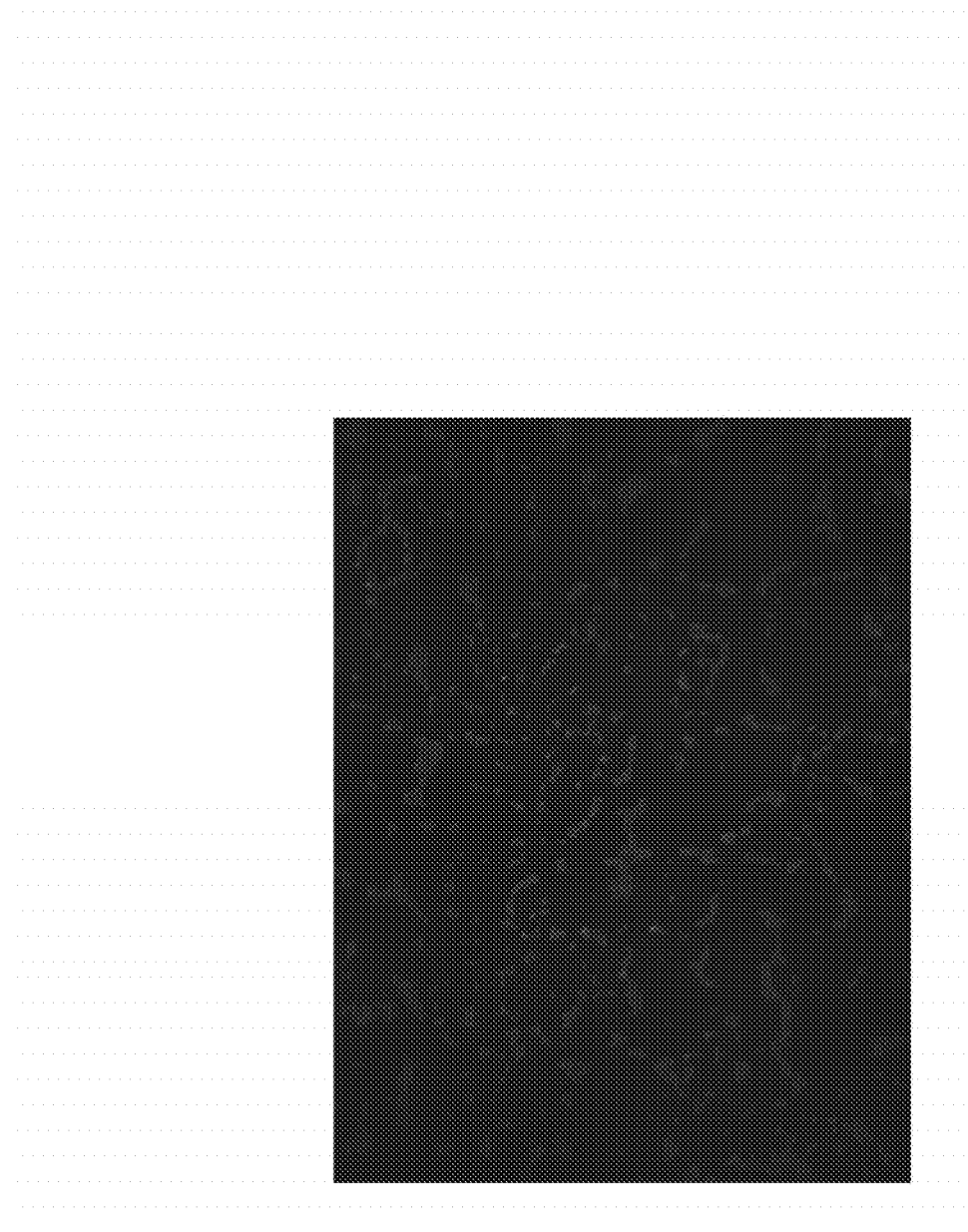
FIG. 14 is a fluorescent image of dried *Escherichia coli* that has not been irradiated with microwave radiation, according to a second comparative example of the present disclosure.
Figure 15:
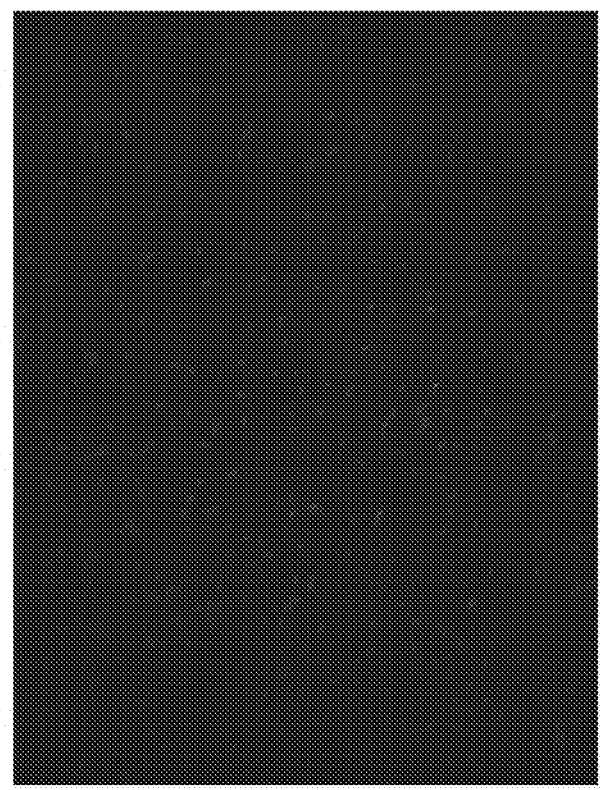
FIG. 15 is a fluorescent image of dried *Escherichia coli* that has been irradiated with microwave radiation, according to a second comparative example of the present disclosure.
Figure 16:
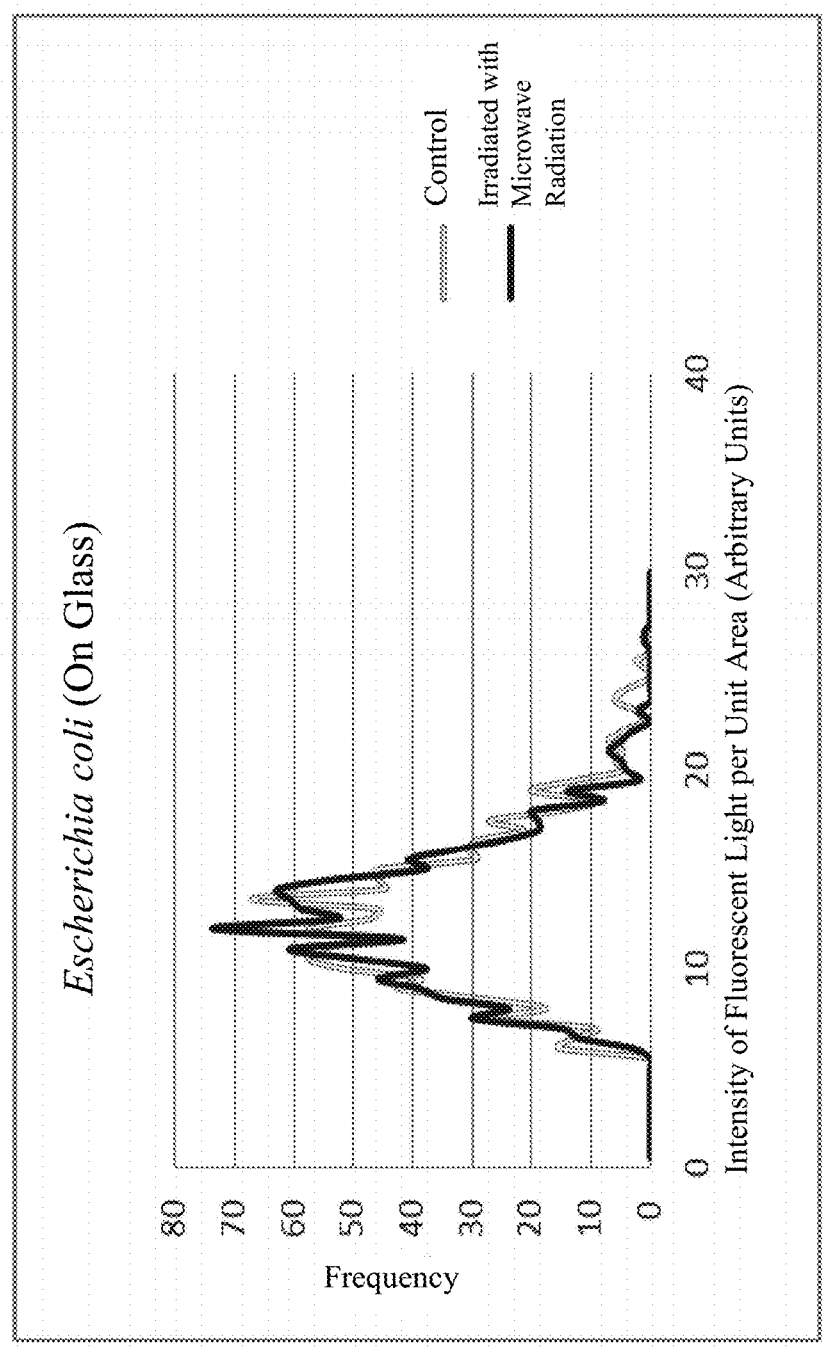
FIG. 16 is a histogram of the fluorescent light intensity distribution of dried *Escherichia coli* that has not been irradiated with microwave radiation, and a histogram of the fluorescent light intensity distribution of dried *Escherichia coli* that has been irradiated with microwave radiation, according to a second comparative example of the present disclosure.

A single-mode resonance resonator was used to irradiate naturally dried *Escherichia coli* on a slide glass for 10 minutes with a 400 W microwave, but no increase in temperature was seen. Thereafter, naturally dried *Escherichia coli* on a slide glass that has not been irradiated with the microwave radiation (a control) and the naturally dried *Escherichia coli* on the slide glass that has been irradiated with the microwave radiation were observed under a fluorescent microscope. The result was the production of the control fluorescent image, shown in FIG. 14, and the fluorescent image of dried *Escherichia coli* that has been irradiated with microwave radiation, shown in FIG. 15. Moreover, when the fluorescent images were analyzed and histograms of the intensities of fluorescent light were produced, no significant difference was seen between the fluorescent intensities of the dried *Escherichia coli* that was irradiated with microwave radiation when compared to those in the control, as illustrated in FIG. 16.

What is claimed is:

1. A fluid-borne microorganism particle detecting device comprising:
   a) a heating flow path through which is configured to flow a liquid that includes microorganism particles;
   b) a microwave emitting device configured to irradiate, with microwave radiation, the liquid that includes the microorganism particles, within the heating flow path;
   c) an inspection flow path connected to the heating flow path;
   d) an excitation beam light source configured to illuminate the inspection flow path with an excitation beam; and
   e) a fluorescence detector configured to detect fluorescent light emitted by the microorganism particles within the inspection flow path that have been illuminated by the excitation beam.

2. The fluid-borne microorganism particle detecting device as set forth in claim 1, further comprising:
   a recirculating flow path configured to return, to the heating flow path, the liquid that includes the microorganism particles, after flowing through the inspection flow path.

3. The fluid-borne microorganism particle detecting device as set forth in claim 2, wherein:
   prior to recirculation by the recirculating flow path, the microwave emitting device does not irradiate, with microwave radiation, the liquid that includes the microorganism particles.

4. The fluid-borne microorganism particle detecting device as set forth in claim 3, wherein:
   after recirculation by the recirculating flow path, the microwave emitting device irradiates, with microwave radiation, the liquid that includes the microorganism particles.

5. The fluid-borne microorganism particle detecting device as set forth in claim 4, further comprising:
   a before/after comparator comparing intensities of fluorescent light emitted by particles prior to recirculation by the recirculating flow path and intensities of fluorescent light emitted by the particles after recirculation by the recirculating flow path.

6. The fluid-borne microorganism particle detecting device as set forth in claim 1, wherein:
   the heating flow path is opaque in respect to light.

7. A fluid-borne microorganism particle detecting method comprising:
   a) irradiating, with the microwave radiation irradiated from the microwave emitting device of the fluid-borne microorganism particle detecting device of claim 1, the liquid that includes the microorganism particles in the heating flow path;
   b) illuminating, by the excitation beam, in the inspection flow path, the microorganism particles that have been irradiated with the microwave radiation; and
   c) detecting fluorescent light emitted by the microorganism particles in the inspection flow path.

8. The fluid-borne microorganism particle detecting method as set forth in claim 7, further comprising:
   prior to irradiation, with microwave radiation, of a liquid that includes microorganism particles, illuminating, with an excitation beam, the microorganism particles that have not been irradiated with the microwave radiation, and
   detecting fluorescent light emitted by the microorganism particles.

9. The fluid-borne microorganism particle detecting method as set forth in claim 8, further comprising:
   comparing intensities of fluorescent light emitted by particles that have not been irradiated with the microwave radiation and intensities of fluorescent light emitted by particles that have been irradiated with the microwave radiation.

10. The fluid-borne microorganism particle detecting method as set forth in claim 9, further comprising:
    evaluating that the particles are microorganism particles if the intensities of the fluorescent light emitted by the particles after irradiation with the microwave radiation are greater than the intensities of the fluorescent light emitted by the particles that have not been irradiated with the microwave radiation.

* * * * *